United States Patent
Olovsson et al.

(10) Patent No.: US 10,197,170 B2
(45) Date of Patent: Feb. 5, 2019

(54) ROTARY VALVE AND SYSTEMS

(71) Applicant: GE HEALTHCARE BIO-SCIENCES AB, Uppsala (SE)

(72) Inventors: Bjorn Markus Olovsson, Uppsala (SE); Christer Olof Eriksson, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 15/533,759

(22) PCT Filed: Dec. 10, 2015

(86) PCT No.: PCT/EP2015/079199
§ 371 (c)(1),
(2) Date: Jun. 7, 2017

(87) PCT Pub. No.: WO2016/096588
PCT Pub. Date: Jun. 23, 2016

(65) Prior Publication Data
US 2017/0321813 A1 Nov. 9, 2017

(30) Foreign Application Priority Data
Dec. 15, 2014 (SE) ........................ 1451539

(51) Int. Cl.
*F16K 5/08* (2006.01)
*F16K 11/083* (2006.01)
(Continued)

(52) U.S. Cl.
CPC ...... *F16K 11/0836* (2013.01); *F16K 11/0743* (2013.01); *F16K 31/041* (2013.01);
(Continued)

(58) Field of Classification Search
CPC ........ F16K 5/08; F16K 11/02; F16K 11/0743; F16K 11/0836; F16K 31/041;
(Continued)

(56) References Cited

U.S. PATENT DOCUMENTS

| 4,158,630 A | * | 6/1979 | Stearns | .................. G01N 30/20 |
| | | | | 210/198.2 |
| 4,569,371 A | | 2/1986 | Dolejs et al. | |

(Continued)

FOREIGN PATENT DOCUMENTS

| EP | 2395351 A1 | 12/2011 |
| WO | 2015/094095 A1 | 6/2015 |
| WO | 2015/094096 A1 | 6/2015 |

OTHER PUBLICATIONS

PCT International Search Report and Written Opinion for PCT Application No. PCT/EP2015/079199 dated Feb. 16, 2016 (12 pages).

(Continued)

*Primary Examiner* — Matthew W Jellett
*Assistant Examiner* — Christopher Ballman
(74) *Attorney, Agent, or Firm* — Eversheds Sutherland (US) LLP (57) ABSTRACT

A rotary valve 1 comprising a stator 3 and a rotor 5, wherein the stator comprises a plurality of connection ports (17a-17l) and orifices (19a-19l) and the rotor comprises a plurality of pairs of rotor valve orifices (23a-23h) joined by transfer channels (25a-25d). The rotor is able to be placed in different working positions whereby fluids can be fed to, for example, chromatography columns and/or can be bypassed through or around the valve. The invention also relates to a system comprising two components such as chromatography columns and a rotary valve.

16 Claims, 11 Drawing Sheets

(51) Int. Cl.
*F16K 11/074* (2006.01)
*G01N 30/20* (2006.01)
*F16K 31/04* (2006.01)
*B01D 15/14* (2006.01)
*F16K 11/02* (2006.01)

(52) U.S. Cl.
CPC ............ *G01N 30/20* (2013.01); *B01D 15/14* (2013.01); *B01D 2201/165* (2013.01); *F16K 5/08* (2013.01); *F16K 11/02* (2013.01); *G01N 2030/201* (2013.01); *G01N 2030/202* (2013.01); *Y10T 137/5762* (2015.04); *Y10T 137/86533* (2015.04); *Y10T 137/86549* (2015.04); *Y10T 137/87442* (2015.04)

(58) Field of Classification Search
CPC .. G01N 30/06; G01N 30/20; G01N 2030/201; G01N 2030/202; B01D 15/14; B01D 2201/165; Y10T 137/5762; Y10T 137/86549; Y10T 137/86533; Y10T 137/87442
See application file for complete search history.

(56) References Cited

U.S. PATENT DOCUMENTS

| | | | |
|---|---|---|---|
| 4,614,204 A | 9/1986 | Dolejs | |
| 4,625,569 A * | 12/1986 | Toei | G01N 35/1097 73/863.72 |
| 4,633,904 A * | 1/1987 | Schumann | F16K 11/074 137/625.11 |
| 4,705,627 A | 11/1987 | Miwa et al. | |
| 5,650,577 A * | 7/1997 | Nagai | F16K 3/36 436/179 |
| 5,958,227 A * | 9/1999 | Uematsu | G01N 30/468 210/198.2 |
| 6,012,488 A * | 1/2000 | Nichols | F16K 11/0743 137/625.11 |
| 6,155,123 A * | 12/2000 | Bakalyar | G01N 30/20 73/61.55 |
| 6,460,349 B1 * | 10/2002 | Kawano | F16K 11/074 251/129.11 |
| 6,874,354 B2 * | 4/2005 | Cueni | G01N 30/20 73/61.55 |
| 8,048,312 B2 * | 11/2011 | Deguchi | G01N 30/20 210/101 |
| 8,186,381 B2 * | 5/2012 | Wilen | F16K 11/074 137/580 |
| 8,225,817 B2 * | 7/2012 | Wilen | F16K 11/0743 137/625.18 |
| 8,434,512 B2 * | 5/2013 | Bergmann | F16K 11/074 137/625 |
| 9,228,982 B2 * | 1/2016 | Ebsen | G01N 30/20 |
| 9,546,646 B2 * | 1/2017 | Stearns | F04B 19/006 |
| 2003/0062084 A1 | 4/2003 | Alhgren et al. | |
| 2010/0032603 A1 | 2/2010 | Wilen | |
| 2012/0125440 A1 | 5/2012 | Price | |
| 2013/0068977 A1 | 3/2013 | Picha et al. | |
| 2013/0174927 A1 | 7/2013 | Wan | |
| 2014/0366739 A1 | 12/2014 | Witt et al. | |

OTHER PUBLICATIONS

PCT International-Type Search Report for ITS/SE14/00278 dated Jul. 3, 2015 (6 pages).

* cited by examiner

ROTARY VALVE AND SYSTEMS

CROSS REFERENCE TO RELATED APPLICATIONS

This application claims the priority benefit of PCT/EP2015/079199 filed on Dec. 10, 2015 which claims priority benefit of Swedish Application No. 1451539-9 filed Dec. 15, 2014. The entire contents of which are hereby incorporated by reference herein.

FIELD OF THE INVENTION

The present invention relates to rotary valves and systems for using such rotary valves.

BACKGROUND

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor. The rotor can be moved from one working position to another working position by hand or by an actuator such as an electric motor.

In general, the stator has a stator body which is provided with a number of inlet and outlet ports connectable to liquid supplies and components which are to be supplied with the liquids, and an end surface with an inner stator face. The ports are in fluid communication with a corresponding set of orifices and/or grooves on the inner stator face via bores in the stator body. The inner stator face is part of the surface of the stator that is in fluid-tight contact with an inner rotor face of the rotor. The rotor is typically formed as a disc and the inner rotor face is pressed against the inner stator face and able to rotate around a, normally central, axis of rotation with respect to the inner stator face. The inner rotor face is provided with one or more grooves and/or orifices which are connected by bores in the rotor body. These grooves and/or orifices can interconnect different orifices and/or grooves on the stator depending on the angular position of the rotor around the axis of rotation with respect to the stator.

Rotary valves can be designed to withstand high pressures (such as pressures above 25 MPa). They can be made from a range of materials, such as stainless steel, high performance polymeric materials and ceramics.

The number of inlets/outlets as well as the design of grooves and bores in the rotor and the stator reflect the intended use of a specific valve. A common type of multipurpose valve has one stator inlet port, placed in the axis of rotation of the rotor of the valve, and a number of outlets ports that are placed equidistantly around the inlet port. The rotor has a single, radially extending groove that has one end in the axis of rotation of the rotor, thereby always being connected to the inlet port of the stator, while the other end can be connected to any one of the outlets by choosing the appropriate the angular position of the rotor with respect to the stator. Such a valve is useful to direct a flow from the inlet to any of the outlets—but only to one outlet at a time.

In many systems, for example, chromatography systems for continuous chromatography, a large number of valves are used for providing two different solutions (e.g. a feed and a buffer) to the different components (e.g. chromatography columns) in the system in the correct order and to guide the solutions leaving the components (e.g. an eluate—the solution of buffer and dissolved matter resulting from elution—and an used feed) to the correct destinations. There is a need for better valve arrangements in such systems.

SUMMARY OF THE INVENTION

One object of the invention is to provide a rotary valve that can be used to provide two liquids to two components, to be able to switch the flow of liquids between the components and subsequently to connect the flows of liquid to two destinations with the possibility to have a bypass around at least one of the components. Such a valve could, for example, be used for continuous chromatography wherein a feed can be switched substantially instantaneously between a first column to a second column of the same type when it is necessary to elute the first column by providing it with buffer solution, and vice versa.

This is achieved in a rotary valve in accordance with the invention comprising a stator with an inner stator face, and a rotor with an inner rotor face arranged in sealing contact with the inner stator face, the rotor being able to be rotated about a rotational axis to a plurality of working positions relative to the inner stator face, the stator comprises a plurality of connection ports each being in fluidic contact with a corresponding valve orifice at the inner stator face and the rotor comprises a plurality of rotor interconnection paths for selective fluidic interconnection of said valve orifices with respect to the rotor position, wherein
the stator comprises at least:
a first fluid inlet connection port able to be connected to a first fluid supply (e.g. a sample feed fluid) for receiving the first fluid,
a second fluid inlet connection port able to be connected to a second fluid supply (e.g. an elution solution such as a buffer) for receiving the second fluid,
a first component return connection port connectable to the outlet of a first component (e.g. a first chromatography column) for receiving fluid from the outlet from the first component,
a second component return connection port connectable to the outlet of a second component (e.g. a second chromatography column) for receiving fluid from the second component,
a first destination outlet connection port connectable to a first destination (for example a sample outlet) for discharging fluid to the first destination
a second destination outlet connection port connectable to a second destination (e.g. an outlet leading eluate to an eluent-receiving arrangement) for discharging fluid to the second destination,
a first feed connection port connectable to the inlet of the first component for feeding fluid to the inlet of the first component, and
a second feed connection port connectable to the inlet of the second component for feeding fluid to the inlet of the second component, and
connection ports for a first bypass loop and a second bypass loop or internal bypass loops,
wherein:
the rotor interconnection paths are arranged to allow the rotor in a first working position:
to interconnect the first fluid inlet connection port with the first component feed connection port,
to interconnect the first component return connection port to the first destination outlet connection port,
to interconnect the second fluid inlet connection port with the second component feed connection port and to interconnect the second component return connection port to the second destination outlet connection port, and wherein the rotor interconnection paths are arranged to allow the rotor in a second working position: to interconnect the first fluid inlet connection port with the second component feed connection port, to interconnect second component return connection port to the first destination outlet connection port, to interconnect the second solution inlet connection port with the first component feed connection port, and, to interconnect the first component return connection port to the second destination outlet connection port, and wherein the rotor interconnection paths are arranged to allow the rotor in a third working position:

to interconnect the first fluid inlet connection port with the first component feed connection port, to interconnect the first component return connection port to the first destination outlet connection port, to interconnect the second fluid inlet connection port with the second destination outlet connection port via a bypass loop without passing through the second component, and wherein the rotor interconnection paths are arranged to allow the rotor in a fourth working position:

to interconnect the first fluid inlet connection port with the second component feed connection port, to interconnect second component return connection port to the first destination outlet connection port, to interconnect the second solution inlet connection port with the second solution outlet connection port via a bypass loop without passing through the first component.

With such a rotary valve, when, for example, used in a continuous chromatography system, in the first working position of the rotary valve a sample from the first fluid, e.g. a sample feed can be loaded onto a first component, e.g. a first column, while any sample loaded onto the second component, e.g. a second column, is eluted from that column by the second fluid. In the second working position of the rotary valve a sample from the sample feed can be loaded onto the second column while any sample loaded onto the first column is eluted from that column. In the third working position of the rotary valve a sample from the sample feed can be loaded onto the first column while the elution solution bypasses both columns and is fed directly downstream, for example to further columns. In the fourth working position of the rotary valve a sample from the sample feed can be loaded onto the second column while the elution solution bypasses both columns and is fed downstream for example to further columns.

A further object of the invention is to provide a system for two fluids and two components (such as filters, beds, columns, etc.) which are to be supplied with fluids, which has a convenient and effective valve arrangement.

This is also achieved in a chromatography system comprising at least two components in the form of chromatography columns wherein each chromatography column has an inlet port and an outlet port, said system further comprising: a rotary valve as defined above wherein the connection ports of the stator are connected to the inlets ports and outlet ports of the at least two columns in the system, to at least a first fluid supply in the form of a sample fluid supply, to at least a second fluid supply in the form of an elution solution supply, to at least one elutant receiving outlet and to at least one other outlet leading to another destination.

Hereby at least two columns and at least two inflows can be connected to the rotary valve and the rotary valve can connect the sample feed inflow to any one of the columns, while at the same time the elution solution is supplied to another one of the columns or the elution solution bypasses all columns and is supplied via the valve to a downstream destination. Hereby a chromatography system with a single rotary valve for continuous chromatography with simultaneous elution or bypass of the elution solution can be obtained. This will give a system with fewer valves and fewer flow connections compared to traditional continuous flow chromatography systems. This will provide a convenient and improved rotary valve and chromatography system.

In one embodiment of the invention the interconnections of the connection ports with each other can be achieved by the rotation of the rotor from one working position to another working position.

In one embodiment of the invention at least two of the rotor interconnection paths are partly radial bores.

In another embodiment of the invention at least two of the stator interconnection paths are partly radial bores arranged to form internal bypass channels.

In one embodiment of the invention at least two of the rotor interconnection paths comprise one annular groove and one radial channel.

In one embodiment of the invention at least two of the stator interconnection paths comprise one annular groove and one radial channel.

In one embodiment of the invention the annular grooves are concentrically positioned around the axis of rotation of the rotary valve.

In one embodiment of the invention additional connection ports are provided in the stator in order to allow additional columns or other components to be connected to it.

In all embodiments of a chromatography system in accordance with the invention it is conceivable that eluent which is leaving, or has left the rotary valve, passes through or by at least one detector.

DETAILED DESCRIPTION OF EMBODIMENTS OF THE INVENTION

In the following the rotary valve and systems and methods for using the rotary valve are described using the example of a continuous flow chromatography system—however the invention is not limited to such systems. It encompasses all systems in which the continuous flow of two fluids, each to a separate component, can be substantially instantaneously swapped between the components by the rotation of the rotor from one working position to another or one of the fluids can be led to one component while the other fluid bypasses both components.

Figure 1:
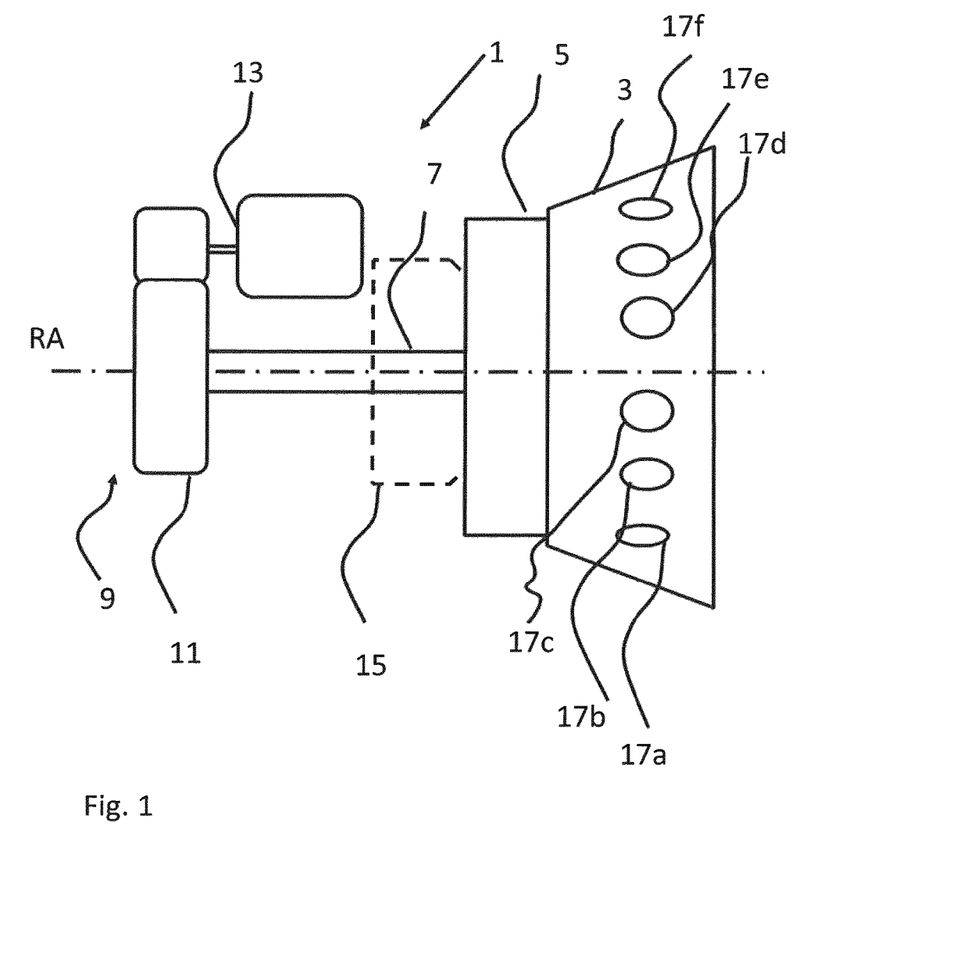
FIG. 1 is a schematic side view of a rotary valve according to one embodiment of the present invention.

The main parts of a typical rotary valve 1 are schematically shown in FIG. 1 (wherein for the sake of clarity brackets, clamps or similar load carrying or fastening elements are omitted). The rotary valve 1 has a stator 3, a rotor 5, a rotatable shaft 7 that optionally may be provided with means (not shown) for recognizing its angular position and a driving unit 9 typically comprising a gearing means 11 and a motor 13 (or, as shown in dashed lines, a manually operable knob 15). The rotor is rotatable with respect to the stator around a rotary axis RA of the valve.

Figure 2:
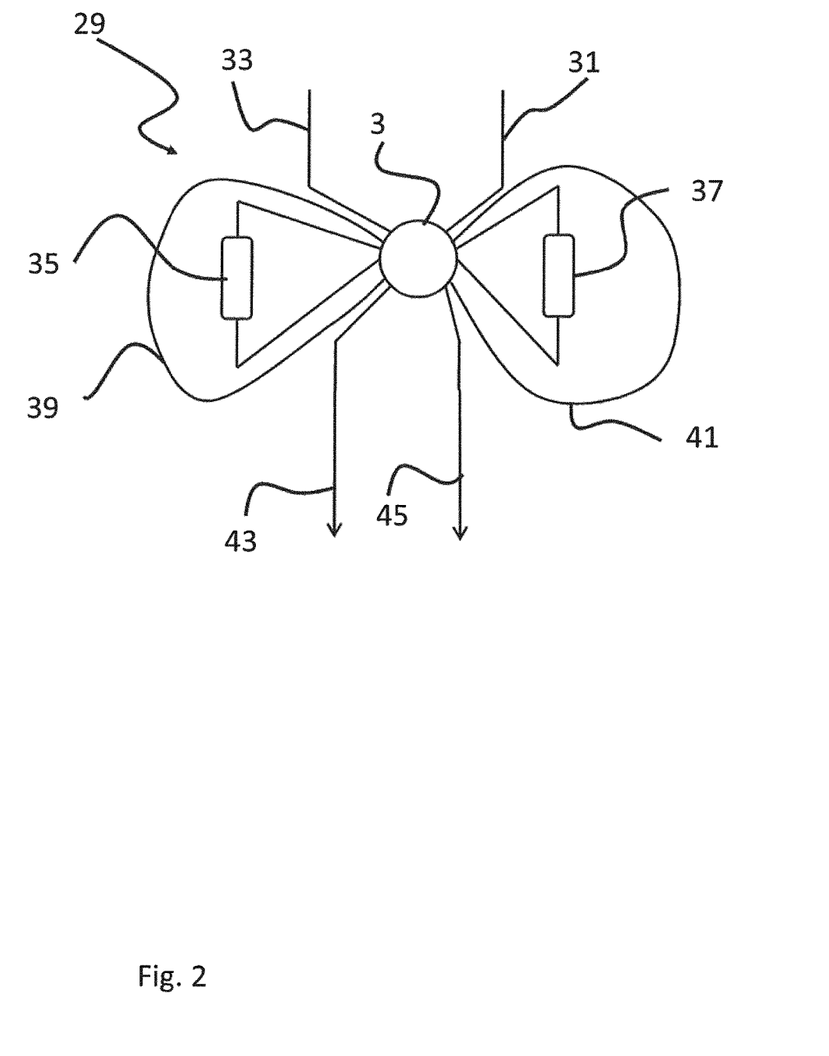
FIG. 2 shows schematically an embodiment of a system in accordance with the present invention with two components in which the rotary valve of the invention can be used.
Figure 3:
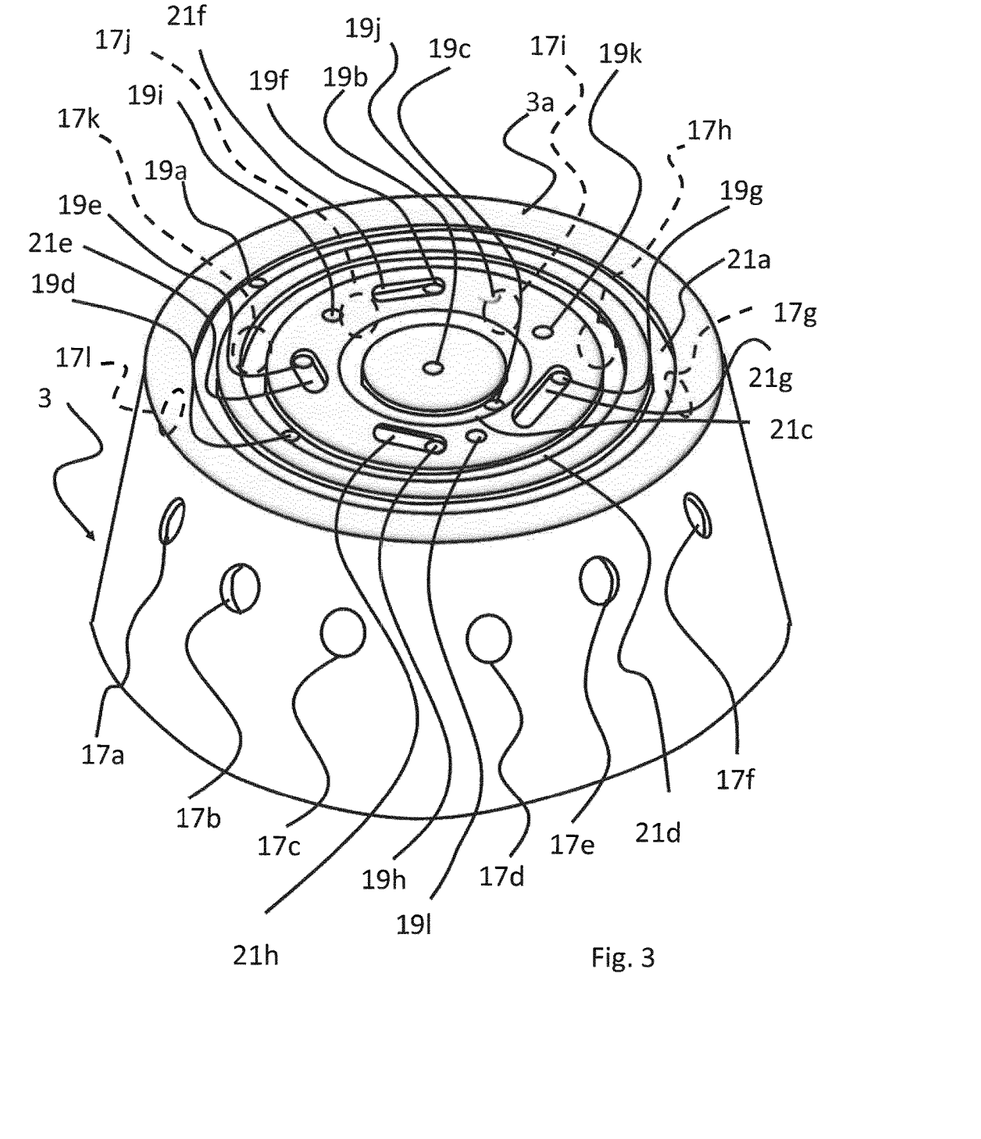
FIG. 3 shows schematically in perspective a stator for a rotary valve according to one embodiment of the invention.

Such a rotary valve can be used in a continuous chromatography system 29 with bypass as shown in FIG. 2. The system comprises a first fluid (e.g. a sample solution) supply 31, a second fluid (e.g. an elution solution) supply 33, a rotary valve 3, a first component (e.g. a chromatography column) 35, a second component (e.g. a chromatography column) 37, a first bypass loop 39, a second bypass loop 41, a first downstream destination 43 and a second downstream destination (e.g. an elutant-receiving path) 45. The sample is fed into the system and loaded onto a first column and the used sample is led from the first column to a first downstream destination, for example a waste drain or a further analysis component or detector. At the same time a second, previously loaded column is eluted by an elution solution (eluent) so that the sample is released from the loaded column (the elutant) and, together with the remains of the elution solution are led to the elutant receiving path 45 where it can be studied or collected or used in some other way e.g. loaded onto a further chromatography column. The stator 3 is provided with twelve connection ports 17a-17l as shown in FIG. 3 which is a perspective view of a stator. These connection ports are arranged to provide for fluid communication with a fluid source or fluid outlet or with any component with which the valve is to co-operate. The ports may be positioned on any suitable part of the stator, and in any suitable direction. The ports are preferably provided with means to ensure the secure connection of capillaries or tubing. Such means may be of any suitable type, such as conventional screw fittings well known to anyone skilled in the art. The ports are in fluid communication via internal channels (not shown) with a set of twelve valve orifices 19a-19l which emerge on the inner stator face 3a, i.e. the surface of the stator that during operation is in contact with the inner rotor face 5a of rotor 5 or in transverse grooves or annular channels 21a, 21c-21g formed in the rotor inner face.

Figure 4:
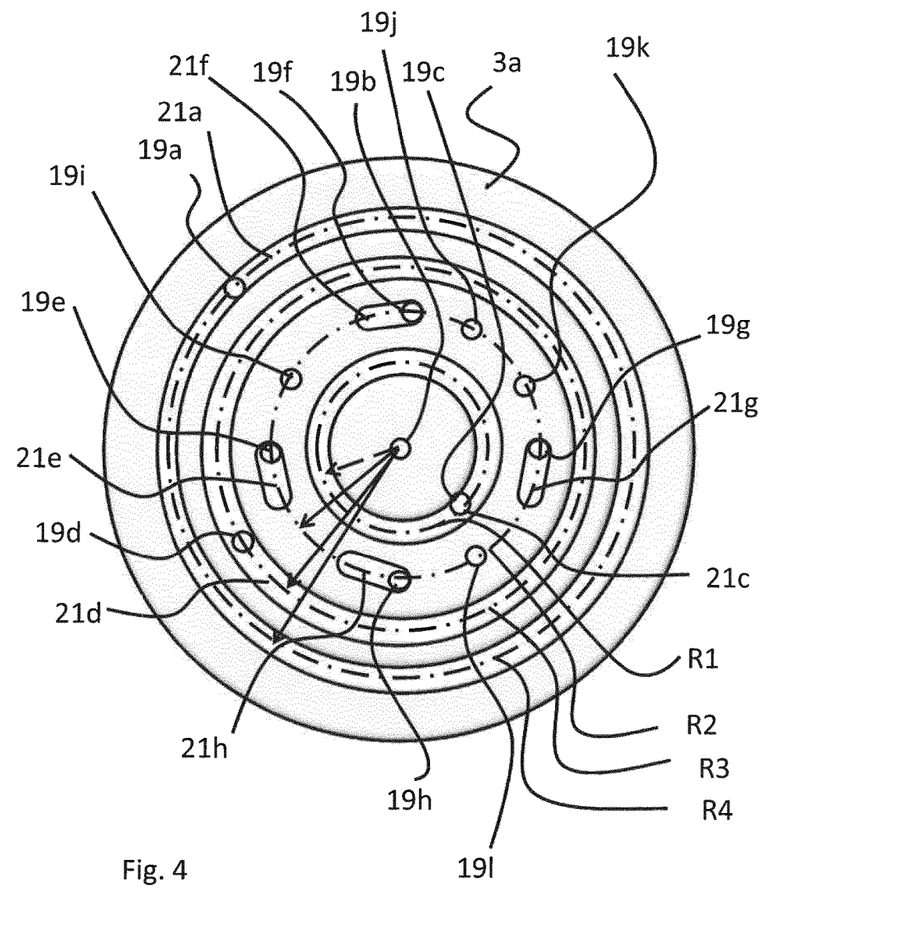
FIG. 4 shows schematically a plan view of the stator face.

During use, fresh elution solution connection port 17a, fresh elution solution valve orifice 19a and fresh elution solution annular channel 21a are in fluid communication with the elution solution supply 33 and provide a path for the fresh elution solution to enter the valve.

During use, used elution solution connection port 17b and used elution solution central valve orifice 19b are in fluid communication and provide a path for the used elution solution to leave the valve to the eluent receiving path 45.

During use, fresh sample feed solution connection port 17c, fresh sample feed solution valve orifice 19c and fresh sample feed solution transverse channel 21c are in fluid communication with the sample feed supply 31 and provide a path for the fresh sample feed solution to enter the valve.

During use, used sample feed solution connection port 17d, used sample feed solution valve orifice 19d and used sample feed solution annular channel 21d are in fluid communication and provide a path for the used sample feed solution to exit the valve to the downstream destination 43.

During use, second chromatography column inlet/feed connection port 17e, second chromatography column inlet/feed valve orifice 19e and second chromatography column inlet/feed transverse channel 21e are in fluid communication with the inlet to the second chromatography column 37 and provide a path for solutions from the valve to enter the second chromatography column.

During use, second chromatography column return connection port 17f, second chromatography column return valve orifice 19f and second chromatography column return transverse channel 21f are in fluid communication with the return outlet from the second chromatography column and provide a path for solutions to return to the valve from the second chromatography column.

During use, first chromatography column inlet/feed connection port 17g, first chromatography column inlet/feed valve orifice 19g and first chromatography column inlet/feed transverse channel 21g are in fluid communication with the inlet to the first chromatography column 35 and provide a path for solutions from the valve to enter the first chromatography column.

During use, first chromatography column return connection port 17h, first chromatography column return valve orifice 19h and first chromatography column return transverse channel 21h are in fluid communication with the return outlet from the first chromatography column and provide a path for solutions to return to the valve from the first chromatography column.

During use, first bypass loop inlet connection port 17i and first bypass loop feed valve orifice 19i are in fluid communication and provide a path for solutions to enter the first bypass loop 39.

During use first bypass loop outlet connection port 17j and first bypass loop return valve orifice 19j are in fluid communication and provide a path for solutions to return from the first bypass loop.

During use, second bypass loop inlet connection port 17k and second bypass loop feed valve orifice 19k are in fluid communication and provide a path for solutions to enter the second bypass loop 41.

During use, second bypass loop outlet connection port 17l and second bypass loop return valve orifice 19l are in fluid communication and provide a path for solutions to return from the second bypass loop.

During use, the annular channels 21a, 21c and 21d and central valve orifice 19b allow the transfer of fluid to or from the respective valve orifice 19a, 19c, 19d over a wide range of angular positions of the rotor with respect to the stator. If an annular channel forms a complete circle then the fluid in it will be accessible in any position of the rotor. The fluid in central orifice also is accessible in any position of the rotor. This allows these channels and orifices to maintain fluid communication for the incoming solutions and for the outgoing solutions to orifices in the rotor in all working positions of the rotor with respect to the stator. The same effect can be achieved with channels which do not form complete circles as long as the circumferential extend of the channels is sufficiently large such that in every appropriate working position of the rotor the desired rotor orifice is over the appropriate channel. The transverse channels $21e$ to $21h$ allow the transfer of fluid to or from the associated valve orifice to a rotor orifice over a limited range of angular positions of the rotor with respect to the stator. The limited range is determined by the angle that the transverse channel subtends and is intended to allow each of the transverse channels to be in fluid contact with a rotor orifice in many working positions of the rotor with respect to the stator. Simple valve orifices $19i$-$19l$ only allow fluid contact with a rotor orifice in a limited number of working positions of the rotor with respect to the stator.

Figure 5:
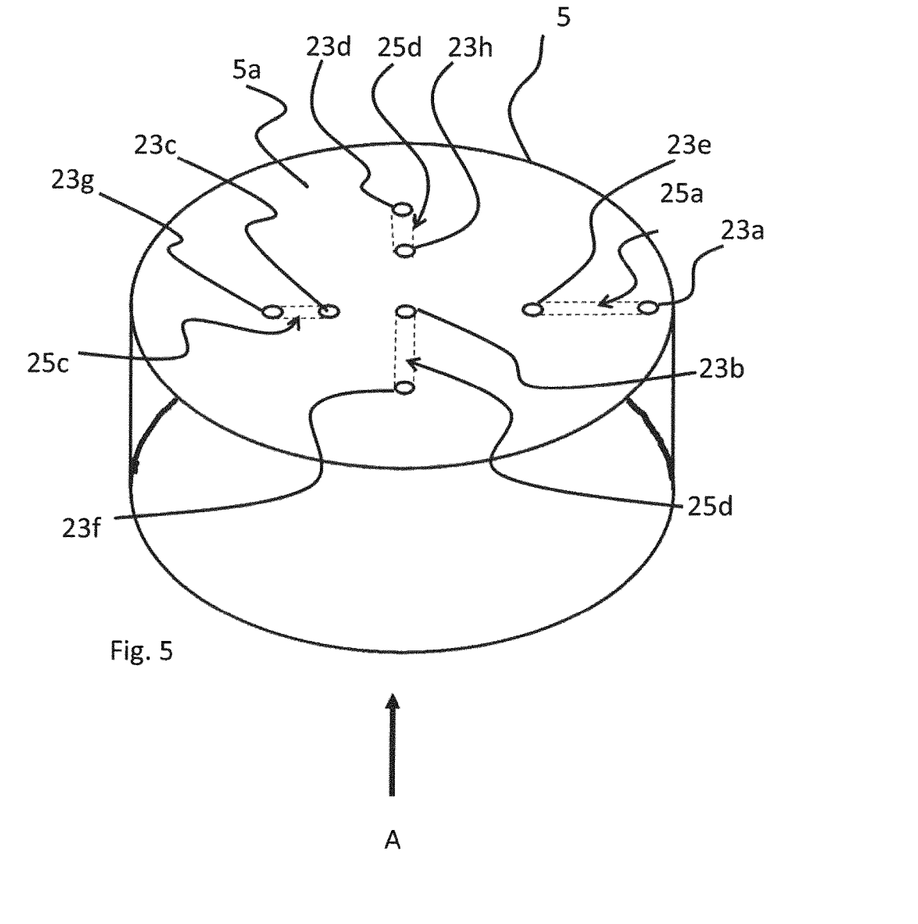
FIG. 5 shows schematically in perspective a rotor of a rotary valve according to one embodiment of the invention.
Figure 6:
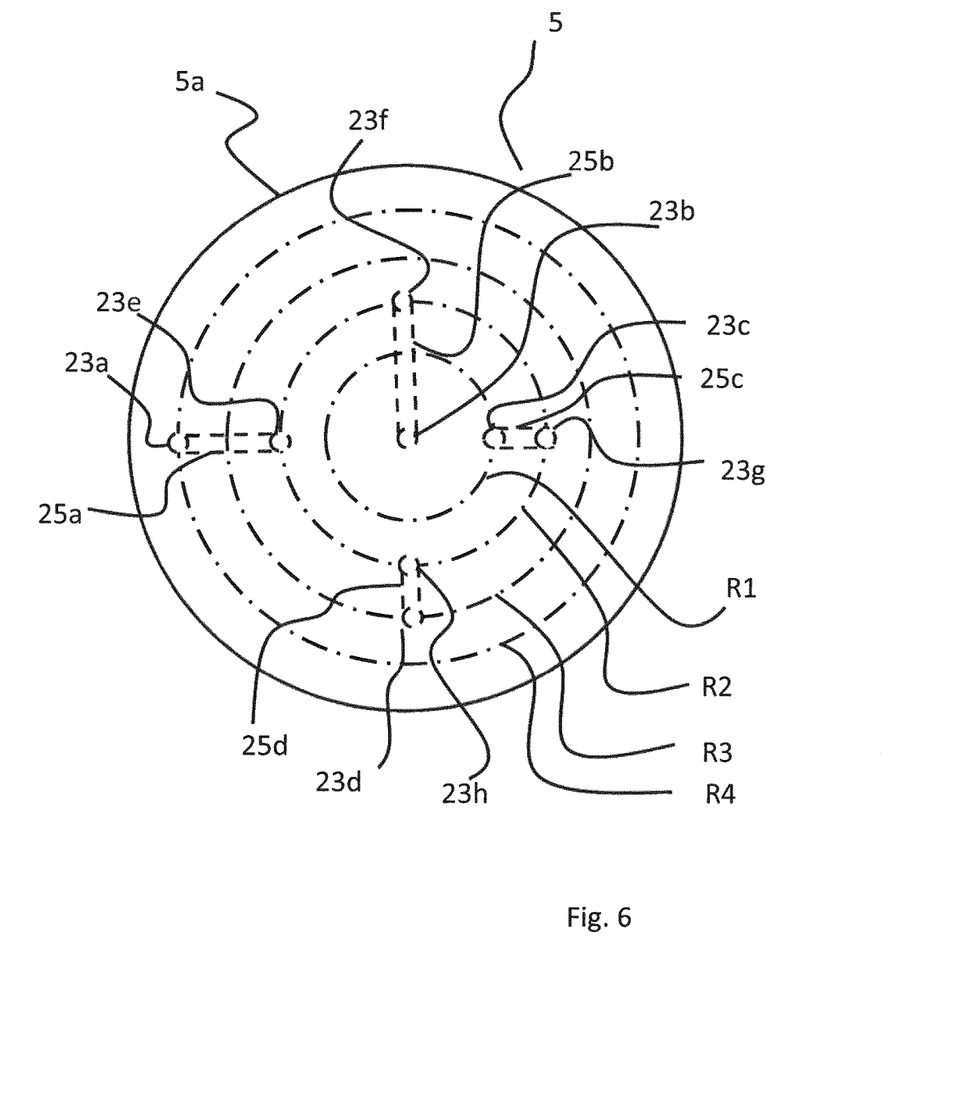
FIG. 6 show schematically the rotor face of the rotor of FIG. 4 from the direction A shown in FIG. 5.

The rotor 5 may be formed as a cylinder or as a disc or the like and has an inner rotor face 5a that is pressed against the flat inner stator face 3a during operation to achieve sealing contact there between. The inner rotor face 5a is provided with eight orifices 23a-23g which are interconnected in pairs by transfer channels 25a to 25d formed in the rotor. These interconnected pairs of orifices and transfer channels can provide interconnection paths that can be used to interconnect the different valve orifices 19a-19l (which open out on the inner stator face 3a) in a plurality of different ways. Different flow paths can be selected by changing the rotary position of the rotor with respect to the stator. The interconnection paths may be any type of path capable of providing fluidic contact between two valve orifices, and, preferably, each comprises an internal channel with discrete orifices.

During use fresh elution solution rotor orifice 23a receives fresh elution solution and fresh elution solution transfer channel 25a transfers the elution solution to fresh elution solution discharge orifice 23e.

During use fresh sample feed solution rotor orifice 23c receives fresh sample feed solution and fresh sample feed solution transfer channel 25c transfers the sample feed solution to fresh feed solution discharge orifice 23g.

During use used elution solution rotor orifice 23f receives used elution solution and used elution solution transfer channel 25b transfers the used elution solution to used elution discharge orifice 23b.

During use used sample feed solution rotor orifice 23h receives used sample feed solution and used sample feed solution transfer channel 25d transfers the used sample feed solution to used feed solution discharge orifice 23d.

Such a system is suitable for continuous chromatography in the case when the elution time from a column is less than the feed time needed to load the column. In such cases it can be undesirable for practical reasons to stop the flow of elution solution and equally undesirable to continue to feed it to the chromatography column. In such cases it is preferable to bypass the columns and supply the elution solution to the downstream arrangement for collecting the eluant. Another reason for bypassing the column is that the elution solution may be needed to elute a further column which is downstream the first two columns. This column requires fresh, unused elution solution and this can be achieved by using the same elution solution feed which bypasses the columns. Naturally the number of columns in a continuous chromatography system or other system can be varied. For example, in the event that the feed time to a column is less than the elution time from a column then in order to allow continuous feeding of the sample to a column during elution a third column or a fourth column or even more columns could be required and other valves would be needed to direct the flows to the relevant column(s). Similarly, if it is desired to use a system with more than two fluids, it is conceivable to provide the system with one or more additional fluid supplies and to connect them by one or more valves to the system.

Figure 7:
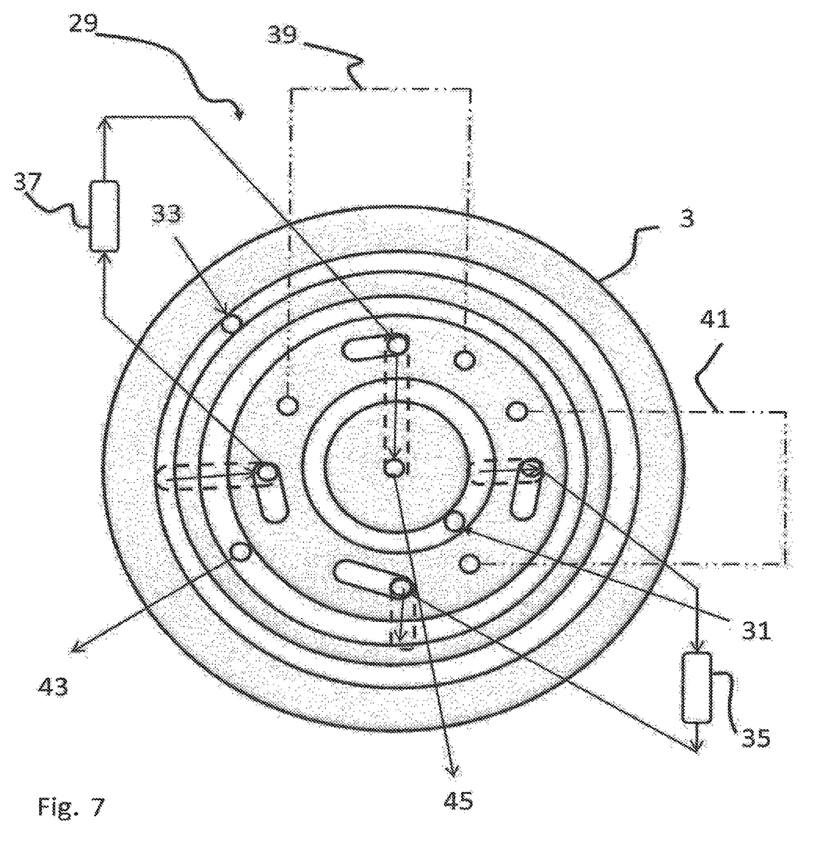
FIG. 7 shows schematically the system of FIG. 2 in which the valve rotor is in a first working position where the first component is being supplied with a first solution while the second component is being provided with a second solution.

FIG. 7 shows the rotor and stator flow paths when the rotor is in a first working position. In the first working position of the rotary valve a sample from the sample feed can be loaded onto a first column while any sample loaded onto the second column is eluted from that column. This is achieved by interconnecting the sample feed inlet connection port with the first column outlet connection port, interconnecting the first column return connection port to the downstream destination outlet connection port, interconnecting the elution solution inlet connection port with the second column outlet connection port, and interconnecting the second column return connection port to the elutate outlet connection port.

Figure 8:
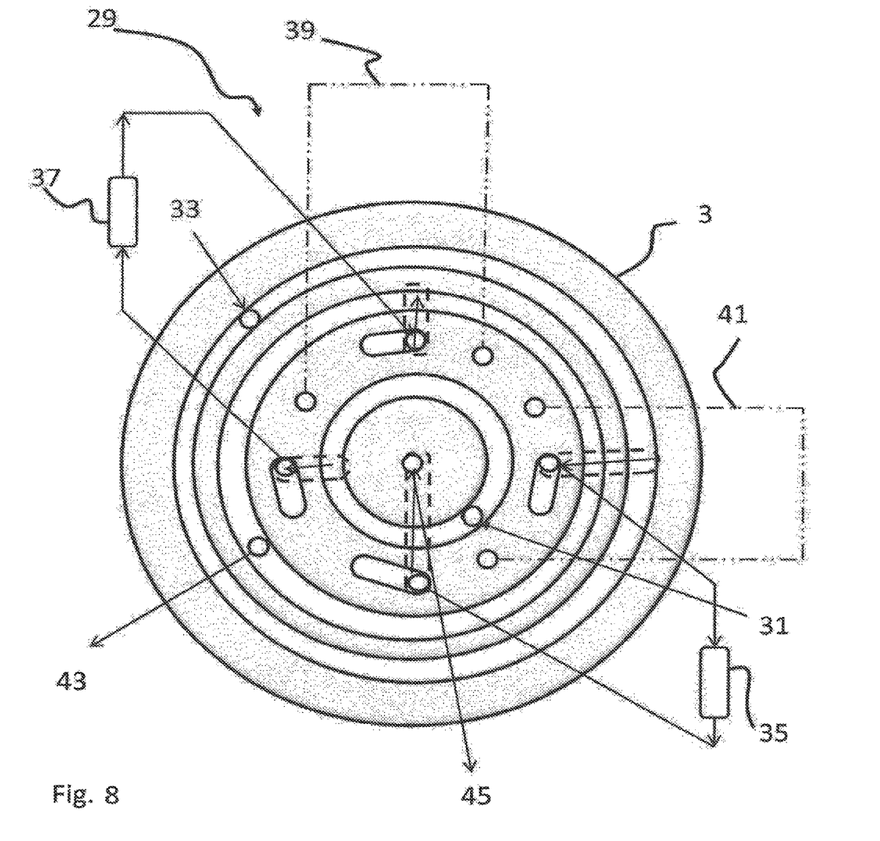
FIG. 8 shows schematically the system of FIG. 2 in which the valve rotor is in a second working position where the second component is being supplied with a first solution while the first component is being provided with a second solution.

FIG. 8 shows the rotor and stator flow paths when the rotor is in a second working position. In the second working position of the rotary valve a sample from the sample feed can be loaded onto a second column while any sample loaded onto the first column is eluted from that column. This is achieved by interconnecting the sample feed inlet connection port with the second column outlet connection port, interconnecting second column return connection port to the downstream destination outlet connection port, interconnecting the elution solution inlet connection port with the first column outlet connection port, and, interconnecting the first column return connection port to the elution outlet connection port.

Figure 9:
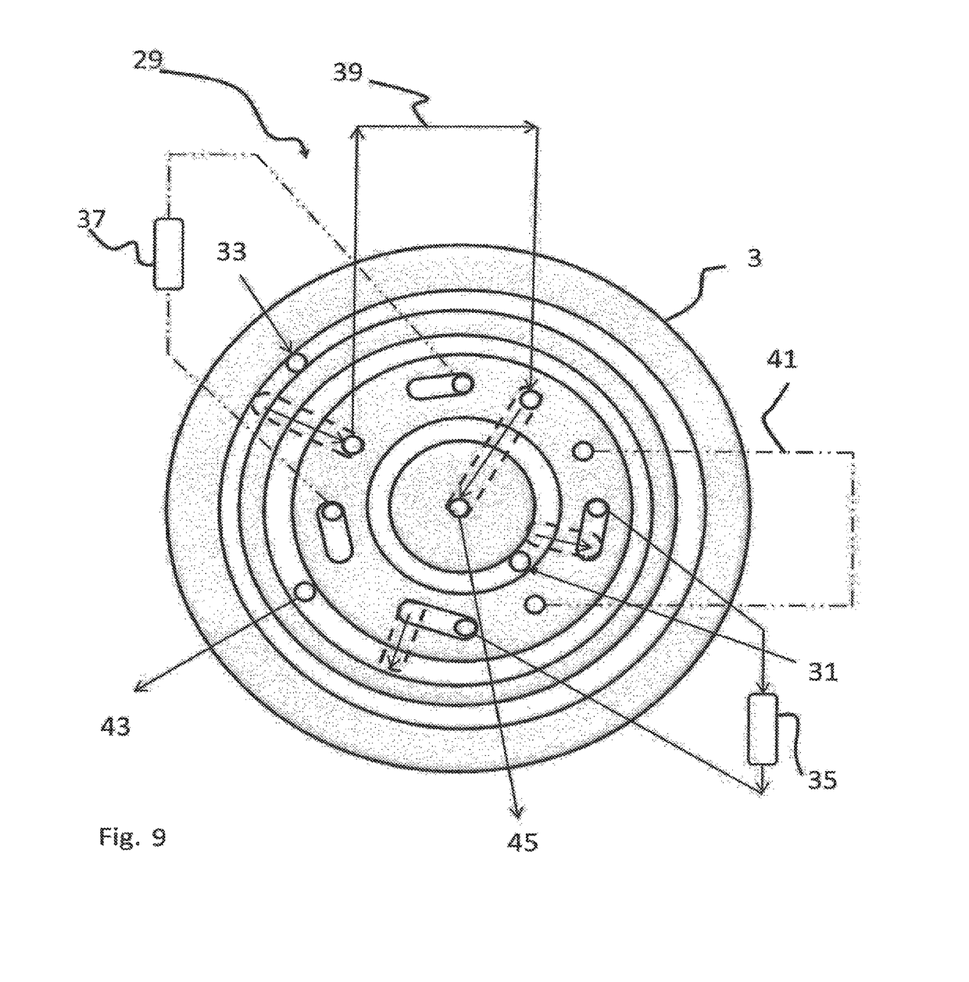
FIG. 9 shows schematically the system of FIG. 2 in which the valve rotor is in a third working position where the first component is being supplied with the first solution while the first bypass is being provided with the second solution.

FIG. 9 shows the rotor and stator flow paths when the rotor is in a third working position. In the third working position of the rotary valve a sample from the sample feed can be loaded onto a first column while the elution fluid bypasses any column and is fed directly to the downstream destination. This is achieved by interconnecting the sample feed inlet connection port with the first column outlet connection port, interconnecting the first column return connection port to the downstream destination outlet connection port, interconnecting the elution solution inlet connection port with the elution outlet connection port via the first bypass loop.

Figure 10:
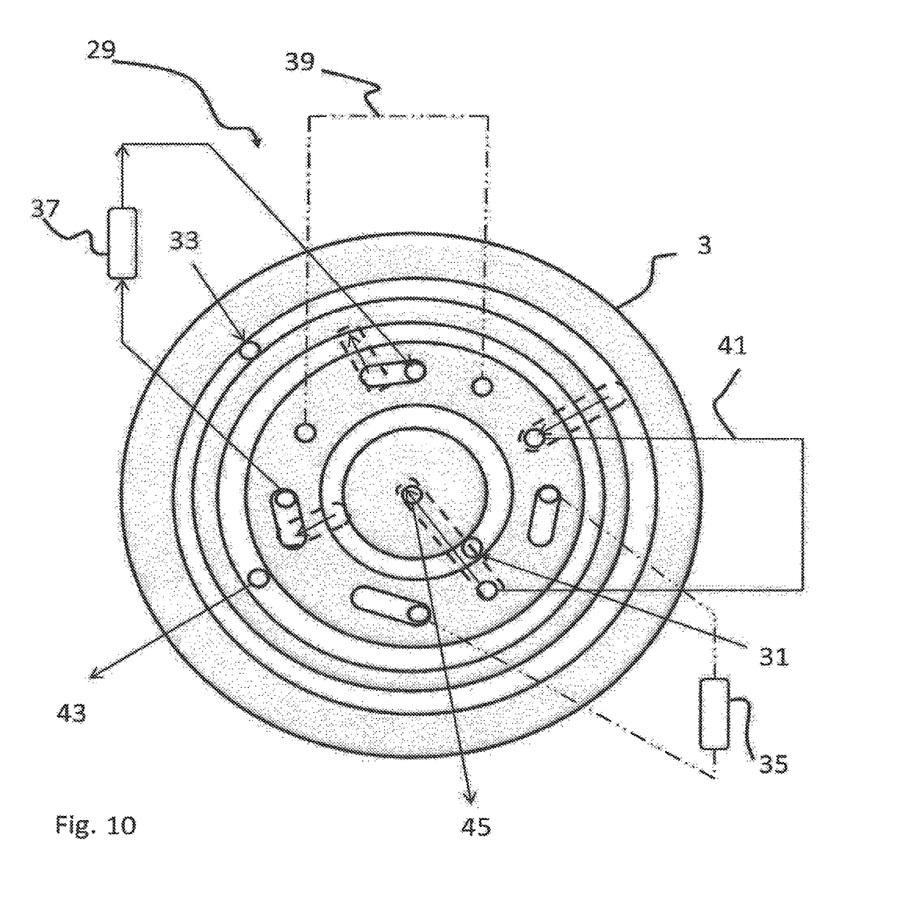
FIG. 10 shows schematically the system of FIG. 2 in which the valve rotor is in a fourth working position where the second component is being supplied with the first solution while the second bypass is being provided with the second solution.

FIG. 10 shows the rotor and stator flow paths when the rotor is in a fourth working position. In the fourth working position of the rotary valve a sample from the sample feed can be loaded onto a second column while the elution fluid bypasses any column and is fed directly to the downstream destination.

This is achieved by interconnecting the sample feed inlet connection port with the second column outlet connection port, interconnecting second column return connection port to the downstream destination outlet connection port, interconnecting the elution solution inlet connection port with the elution outlet connection port via the second bypass loop.

Figure 11:
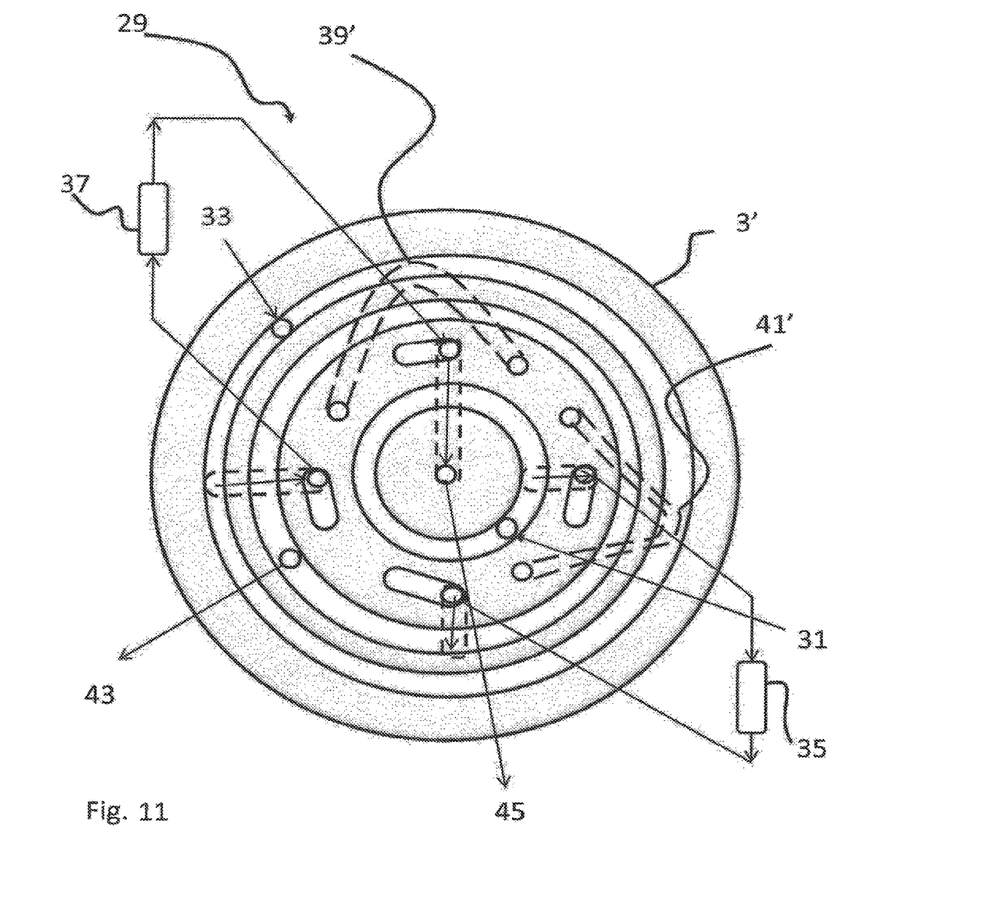
FIG. 11 shows schematically a second embodiment of the stator of a rotary valve in accordance with the present invention in which the valve stator is provided with a first internal bypass loop and a second internal bypass loop.

FIG. 11 shows a second embodiment of stator 3' a rotary valve in accordance with the present invention in which the valve stator is provided with a first internal bypass loop 39' and a second internal bypass loop 41'. In all other aspects the second embodiment of the invention is essentially the same as the first embodiment of the invention.

The above mentioned example of conceivable embodiments are intended to illustrate the present invention and are not intended to limit the scope of protection claimed by the following claims.

The invention claimed is:

1. A rotary valve comprising a stator with an inner stator face, and a rotor with an inner rotor face arranged in sealing contact with the inner stator face, the rotor being able to be rotated about a rotational axis to a plurality of working positions relative to the inner stator face, the stator comprises a plurality of connection ports each being in fluidic contact with a corresponding valve orifice at the inner stator face and the rotor comprises a plurality of rotor interconnection paths for selective fluidic interconnection of said valve orifices with respect to the rotor position, wherein
the stator comprises at least:
a first fluid inlet connection port connectable to a first fluid supply for receiving a first fluid,
at least a second fluid inlet connection port connectable to a second fluid supply for receiving a second fluid,
a first component return connection port connectable to a first component for receiving fluid from an outlet of a first component,
a second component return connection port connectable to a second component for receiving fluid from an outlet of a second component,
a first destination outlet connection port connectable to a first destination for discharging fluid to a first destination,
a second destination outlet connection port connectable to a second destination for discharging fluid to a second destination,
a first feed connection port connectable to an inlet of a first component, and a first feed angular transverse channel connectable in fluid communication with the inlet to the first component for feeding fluid to the inlet of the first component,
a second feed connection port connectable to an inlet of a second component, and a second feed angular transverse channel connectable in fluid communication with the inlet to the second component for feeding fluid to the inlet of the second component, and
wherein the stator further comprises:
an outlet connection port connectable to an inlet of a first external bypass loop for feeding fluid to an external first bypass loop, an inlet connection port connectable to an outlet of an external first bypass loop for receiving fluid from the first bypass loop, an outlet connection port connectable to an inlet of a second external bypass loop for feeding fluid to the external second bypass loop and an inlet connection port connectable to an outlet of a second external bypass loop for receiving fluid from the second bypass loop, and
wherein the rotor interconnection paths comprise channels and orifices which are arranged to allow the rotor in a first working position:
to interconnect the first fluid inlet connection port with the first component feed connection port,
to interconnect the first component inlet connection port to the first destination outlet connection port,
to interconnect the second fluid inlet connection port with the second component feed connection port and to interconnect the second component inlet connection port to the second destination outlet connection port; and the rotor interconnection paths are arranged to allow the rotor in a second working position:
to interconnect the first fluid inlet connection port with the second component feed connection port,
to interconnect second component inlet connection port to the first destination outlet connection port,
to interconnect the second solution inlet connection port with the first component feed connection port, and,
to interconnect the first component inlet connection port to the second destination outlet connection port; and
the rotor interconnection paths are arranged to allow the rotor in a third working position:
to interconnect the first fluid inlet connection port with the first component feed connection port,
to interconnect the first component inlet connection port to the first destination outlet connection port,
to interconnect the second fluid inlet connection port with the second destination outlet connection port via a bypass loop without passing through the second component; and,
the rotor interconnection paths are arranged to allow the rotor in a fourth working position:
to interconnect the first fluid inlet connection port with the second component feed connection port,
to interconnect second component inlet connection port to the first destination outlet connection port,
to interconnect the second solution inlet connection port with the second solution outlet connection port via a bypass loop without passing through the first component; and
wherein the angular transverse channels allow the transfer of fluid over a range of angular positions of the rotor with respect to the stator.

2. The rotary valve of claim 1, wherein the stator comprises a central orifice on the stator inner face.

3. A rotary valve of claim 2 wherein at least one concentric annular groove is continuous.

4. The rotary valve of claim 1, wherein the stator inner face comprises three concentric annular grooves.

5. A system comprising a rotary valve of claim 1, wherein said rotary valve is in fluid connection with a first fluid supply, a second fluid supply and two components.

6. A chromatography system comprising a rotary valve of claim 1, wherein said rotary valve is in fluid connection with a first fluid supply, a second fluid supply and two chromatography columns.

7. A chromatography system of claim 6 further comprising two external bypass loops which bypass said chromatography columns.

8. The use of a rotary valve comprising using the rotary valve of claim 1 in a system comprising a rotary valve, wherein said rotary valve is in fluid connection with a first fluid supply, a second fluid supply and two chromatography columns.

9. A rotary valve comprising a stator with an inner stator face, and a rotor with an inner rotor face arranged in sealing contact with the inner stator face, the rotor being able to be rotated about a rotational axis to a plurality of working positions relative to the inner stator face, the stator comprises a plurality of connection ports each being in fluidic contact with a corresponding valve orifice at the inner stator face and the rotor comprises a plurality of rotor interconnection paths for selective fluidic interconnection of said valve orifices with respect to the rotor position, wherein
the stator comprises at least:
a first fluid inlet connection port connectable to a first fluid supply for receiving a first fluid, at least a second fluid inlet connection port connectable to a second fluid supply for receiving a second fluid, a first component return connection port connectable to a first component for receiving fluid from an outlet of a first component, a second component return connection port connectable to a second component for receiving fluid from an outlet of a second component, a first destination outlet connection port connectable to a first destination for discharging fluid to a first destination, a second destination outlet connection port connectable to a second destination for discharging fluid to a second destination, a first feed connection port connectable to an inlet of a first component, and a first feed angular transverse channel connectable in fluid communication with the inlet to the first component for feeding fluid to the inlet of the first component, a second feed connection port connectable to an inlet of a second component, and a second feed angular transverse channel connectable in fluid communication with the inlet to the second component for feeding fluid to the inlet of the second component, and wherein the stator further comprises:

an internal first bypass loop and an internal second bypass loop; and wherein the rotor interconnection paths comprise channels and orifices which are arranged to allow the rotor in a first working position:

to interconnect the first fluid inlet connection port with the first component feed connection port, to interconnect the first component inlet connection port to the first destination outlet connection port, to interconnect the second fluid inlet connection port with the second component feed connection port and to interconnect the second component inlet connection port to the second destination outlet connection port; and the rotor interconnection paths are arranged to allow the rotor in a second working position:

to interconnect the first fluid inlet connection port with the second component feed connection port, to interconnect second component inlet connection port to the first destination outlet connection port, to interconnect the second solution inlet connection port with the first component feed connection port, and, to interconnect the first component inlet connection port to the second destination outlet connection port; and the rotor interconnection paths are arranged to allow the rotor in a third working position:

to interconnect the first fluid inlet connection port with the first component feed connection port, to interconnect the first component inlet connection port to the first destination outlet connection port, to interconnect the second fluid inlet connection port with the second destination outlet connection port via a bypass loop without passing through the second component; and, the rotor interconnection paths are arranged to allow the rotor in a fourth working position:

to interconnect the first fluid inlet connection port with the second component feed connection port, to interconnect second component inlet connection port to the first destination outlet connection port, to interconnect the second solution inlet connection port with the second solution outlet connection port via a bypass loop without passing through the first component; and wherein the angular transverse channels allow the transfer of fluid over a range of angular positions of the rotor with respect to the stator.

10. The rotary valve of claim 9, wherein the stator comprises a central orifice on the stator inner face.

11. The rotary valve of claim 9, wherein the stator inner face comprises three concentric annular grooves.

12. A rotary valve of claim 9, wherein at least one concentric annular groove is continuous.

13. A system comprising a rotary valve of claim 9, wherein said rotary valve is in fluid connection with a first fluid supply, a second fluid supply and two components.

14. A chromatography system comprising a rotary valve of claim 9, wherein said rotary valve is in fluid connection with a first fluid supply, a second fluid supply and two chromatography columns.

15. A chromatography system of claim 14 further comprising two external bypass loops which bypass said chromatography columns.

16. The use of a rotary valve comprising using the rotary valve of claim 9.

* * * * *